(12) United States Patent
Rupprecht et al.

(10) Patent No.: US 6,780,504 B2
(45) Date of Patent: Aug. 24, 2004

(54) ACTIVE SUBSTANCE-CONTAINING MULTI-LAYER FILM OF HYDROPHILIC POLYMERS CROSSLINKED IN SITU

(75) Inventors: Herbert Rupprecht, Regensburg (DE); Stephan Zinzen, Hamburg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/043,267

(22) Filed: Jan. 14, 2002

(65) Prior Publication Data

US 2002/0142036 A1 Oct. 3, 2002

Related U.S. Application Data

(63) Continuation of application No. PCT/EP00/05824, filed on Jun. 23, 2000.

(30) Foreign Application Priority Data

Jul. 13, 1999 (DE) .......................................... 199 32 603

(51) Int. Cl.[7] .................................................. A61K 9/70
(52) U.S. Cl. ................. 428/354; 343/409; 343/355 CP; 343/355 AK; 343/532; 424/443; 424/447; 424/448; 424/449; 427/2.31
(58) Field of Search ................................ 428/409, 343, 428/354, 355 CP, 355 AK, 532; 427/2.31; 424/443, 447, 448, 449

(56) References Cited

U.S. PATENT DOCUMENTS

| 4,199,569 A | 4/1980 | Chabala et al. |
| 4,389,397 A | 6/1983 | Lo et al. |
| 5,049,395 A | 9/1991 | Chang ........................ 424/494 |
| 5,641,504 A | 6/1997 | Lee et al. |
| 5,667,798 A | * 9/1997 | Royds et al. ................ 424/449 |
| 6,379,691 B1 | 4/2002 | Tedeschi et al. ............. 424/423 |

FOREIGN PATENT DOCUMENTS

| DE | 3128815 | 1/1984 |
| DE | 4242015 | 10/1993 |
| DE | 19532489 | 3/1997 |
| EP | 0251476 | 2/1993 |
| EP | 0630647 | 3/1999 |
| WO | WO 01/03917 A2 | 1/2001 |

OTHER PUBLICATIONS

H. Rupprecht, et al., "Drug Release Regulation by In Situ Crosslinked Films Based on Hydrophilic Polymers" The Second Central European Symposium on Parmaceutical Technology, 1997.
W. C. Campbell, et al., "Ivermectin: A Potent New Anti-parasitic Agent" Science, vol. 221, Aug. 1983.
Ansley J. Coale, "Recent Trends in Fertility in Less Developed Countries" Science, vol. 221, Aug. 1983.
C. B. Abletshauer, et al., "Film coating of pellets with insluble polymers obtained in situ crosslinking in the the fluidized bed" Journal of Controlled Release, vol. 27, 1993.
C. Abletshauer, et al., "Self supporting polymer films crosslinked in situ by simultaneous spraying of component solutions I. Characterization and drug diffusion" Farm vestn, vol. 45, 1994.

* cited by examiner

*Primary Examiner*—D. Lawrence Tarazano
(74) *Attorney, Agent, or Firm*—Crowell & Moring LLP

(57) ABSTRACT

A multi-layered film which contains an active substance and which is made of film-forming polymers. The film comprises at least one covering layer, at least one layer containing the active substance, and an adhesive layer. A method and apparatus for producing such a multi-layered film and a preferred use as a transmucosal galenic formulation are also disclosed.

20 Claims, No Drawings

ACTIVE SUBSTANCE-CONTAINING MULTI-LAYER FILM OF HYDROPHILIC POLYMERS CROSSLINKED IN SITU

CROSS REFERENCE TO RELATED APPLICATIONS

This application is a continuation of international patent application no. PCT/EP00/05824, filed Jun. 23, 2000, designating the United States of America, the entire disclosure of which is incorporated herein by reference. Priority is claimed based on Federal Republic of Germany patent application no. 199 32 603.7, filed Jul. 13, 1999.

BACKGROUND OF THE INVENTION

The present invention relates to an active substance-containing multi-layer film of film-forming polymers with a cover layer, at least one active substance-containing layer and an adherent layer, a process and a device for its production, as well as its use.

The release of active substances from active substance-containing multi-layer films is nowadays becoming increasingly important. These multi-layer films consist of a cover layer that protects the multi-layer film against, inter alia, undesirable influences, an active substance-containing layer and an adherent layer by means of which the multi-layer film is secured to the site at which the active substance is to be released.

In particular the administration of medicaments via transmucosal application by means of a multi-layer film has proved very effective both for local therapy as well as systemic therapy.

The production of films that satisfy the requirements for use in the buccal cavity as regards thickness, flexibility, mucoadhesion, control of the release of active substances and compatibility has however up to now encountered serious technological difficulties. Thus for example, in order to maintain the long-term effect an insolubility in the aqueous medium of the application site is required, especially moreover as regards the cover layer. This necessitates the use of water-insoluble polymers such as for example ethylcellulose, poly(methyl methacrylates), etc.; in other words, substances that can be suitably processed only in organic solvents or in the form of complicated latex or pseudolatex dispersions, which however leads to both ecological and economic disadvantages. Since these multi-layer films are in this connection produced by a casting process, considerable problems moreover also arise in the scaling-up of the production process from the laboratory to the mass production level.

SUMMARY OF THE INVENTION

It is an object of the invention to provide an improved multi-layer film containing at least one active substance, as well as a process and an apparatus for producing such a film.

Another object of the invention is to provide a multi-layer film containing at least one active substance which avoids or overcomes the disadvantages of the prior art, as well as a process and an apparatus for producing such a film.

These an other objects are achieved in accordance with the present invention by providing a multi-layer film of film-forming polymers comprising a cover layer, at least one active substance-containing layer and an adherent layer, wherein the cover layer and/or the active substance-containing layer consists of hydrophilic polymers crosslinked in situ that are no longer water-soluble or are possibly only still water-swellable.

As used herein, the term "crosslinked in situ" means that the film-forming polymer and a suitable crosslinking agent are applied separately from one another to a preferably smooth surface where they are mixed, resulting in an in situ crosslinking after they have been mixed.

The cover layer serves to mechanically stabilize the multi-layer film, to protect the active substance incorporated in the active substance-containing layer, and also as a barrier to prevent diffusion of the active substance, so that a unidirectional release of the active substance takes place through the adherent layer to the site where the multi-layer film is attached.

The cover layer may be produced from any known suitable film-forming, water-soluble polymer(s) and suitable crosslinking agent(s). Suitable polymers and crosslinking agents are disclosed, for example, in Abletshauser, C.; Schneider, R.; Rupprecht, H.: Film coating of pellets with insoluble polymers obtained by "in situ" crosslinking in the fluidized bed, J. Control. Rel. 27, 149–156 (1993) or in Abletshauser, C.; Rupprecht, H.: Self supporting polymer films crosslinked "in situ" by simultaneous spraying of component solutions, Farm. Vestn. 45, 297–309 (1994), which are incorporated herein by reference and are thus part of the disclosure.

Preferably, however, the cover layer is based on cellulose ethers, preferably hydroxyethylcellulose and/or methylcellulose, particularly preferably methylhydroxypropylcellulose. The cellulose ethers are preferably crosslinked with phenolic substances, particularly preferably with tannin. In order to optimize the film properties, the quantitative ratio of polymer to crosslinking agent may be varied in a wide range. Preferably the quantitative ratio is however 4:1 to 1:1. Most particularly preferably the cover layer is based on methylhydroxypropylcellulose crosslinked with tannin, the quantitative ratio being between 4:1 and 1:2.

Also, the cover layer may preferably be based on anionic polymers, preferably sodium carboxymethylcellulose, polyacrylates or carragenates, particularly preferably sodium alginate. The anionic polymers preferably are crosslinked with inorganic ions, particularly preferably calcium ions, or preferably with polycations, particularly preferably chitosan.

Further preferred cover layer materials are films formed from mixtures of methylhydroxypropylcellulose crosslinked with tannin together with latex dispersions of ethylcellulose, suitable poly(methyl methacrylates) such as for example Eudragit RS, Eudragit E, etc., from Röhm Pharma GmbH, Darmstadt, Germany.

Particularly preferred as cover layers also include prefabricated sheets of water-impermeable materials with hydrophobic surfaces, such as polyamides. The cover layer may also be produced from a mixture of polymers in order for example to optimize the properties of this layer.

The function of the cover layer can according to the invention be expanded further by incorporating colored pigments such as for example iron oxides, titanium oxide, etc. and/or sweetening agents and/or aromas, as well as optionally by further auxiliary substances in order to optimize the properties of use, preferably as a medicament form.

Preferably the layer thickness of the cover layer is between 30 and 100 $\mu$m, particularly preferably between 40 and 60 $\mu$m.

The multi-layer film has according to the invention at least one active substance-containing layer that is joined directly to the cover layer. This layer serves according to the invention as an active substance matrix.

The active substance-containing layer may be produced from a suitable film-forming, water-soluble polymer and suitable crosslinking agents, such as are described for example in Abletshauser, C.; Schneider, R.; Rupprecht, H.: Film coating of pellets with insoluble polymers obtained by "in situ" crosslinking in the fluidized bed. J. Control. Rel. 27, 149–156 (1993) or in Abletshauser, C.; Rupprecht, H.: Self supporting polymer films crosslinked "in situ" by simultaneous spraying of component solutions. Farm. Vestn. 45, 297–309 (1994), which are included here by way of reference and are thus part of the disclosure.

Preferably, however, the active substance-containing layer is based on cellulose ethers, preferably hydroxyethylcellulose and/or methylcellulose, particularly preferably methylhydroxypropylcellulose. The cellulose ethers preferably are crosslinked with phenolic substances, particularly preferably with tannin.

In order to optimize the film properties, the quantitative ratio of polymer to crosslinking agent may be varied over a wide range. Preferably, however, the quantitative ratio is from 4:1 to 1:1.

Also preferably, the active substance-containing layer is based on anionic polymers, preferably sodium carboxymethylcellulose, polyacrylates or carragenates, particularly preferably sodium alginate. The anionic polymers preferably are crosslinked with inorganic ions, particularly preferably calcium ions, or with polycations, particularly preferably chitosan.

The active substance-containing layer may also be produced from a mixture of polymers in order for example to optimize the release of active substance from this layer and/or its stability. Preferably the active substance-containing layer is based on methylhydroxypropylcellulose crosslinked with tannin, to which are added further polymers, preferably alginate crosslinked with calcium ions, particularly preferably polyacrylic acid (e.g. Carpol 934 P from BF Goodrich, Cleveland, Ohio, USA) in amounts of 5–50 wt. % relative to the polymer of the active substance-containing layer, for example methylhydroxypropylcellulose, in order to control the release of active substance and improve adhesion to the cover layer and/or adherent layer.

The multi-layer film according to the invention comprises one or more active substance-containing layers. These layers preferably contain the same active substance, each layer having a different respective release profile. Also preferably, these layers optionally may each contain several active substances, and the respective layers may moreover each exhibit different release profiles, if desired.

In the respective active substance-containing layers, the active substance(s) is/are preferably distributed uniformly over substantially the whole layer. Also preferably, the active substance-containing layer moreover exhibits horizontal and/or vertical gradients of the respective active substance(s). Also preferably, the respect active substance is concentrated in specific horizontal and/or vertical segments of the active substance-containing layer.

In order to achieve a specific release profile, for example, it may be desirable to have partial layers free of active substance.

In accordance with the invention, the thickness of the active substance-containing layer may be matched to the amount of active substance to be incorporated. Preferably the layer thickness of each of the active substance-containing layers is between 30 and 100 µm, particularly preferably between 40 and 60 µm.

In principle, there is no restriction on the active substances contained in the active substance-containing layer. Preferably however, the active substances are aromatic principles, aroma substances, diagnostic agents, plant protection agents, pharmaceutical active substances, vitamins, nutrients and/or fertilizers. Suitable pharmaceutical active substances include analgesics, antiallergic agents, antibiotics, antiemetics, antiseptics, antihistamines, antihypertensive agents, appetite suppressants, cardiac agents, chemotherapeutics, enzyme preparations, hormones, immunomodulators, local anaesthetics, psychopharmaceuticals, spasmolytics, virustatics, vitamins and cytostatics.

Suitable active substances also include diamorphine, alflentanil, sufentanyl, pentazocin, buprenorphin, nefopam, flupirtin, tramadol, oxycodon, metamizol, propyphenanzone, phenazone, nifenazone, phenylbutazone, oxyphenbutazone, mofebutazone, diflunisal, meptazinol, methadone, pethidine, meloxicam, fenbufen, mefenamic acid, tenoxicam, azapropazon, piritramide, tramadol, amantadine, benzotropine, procyclidine, moclobemide, tranylcypromide, maprotilin, doxepine, opipramol, desipramine, imipramine, fluroxamine, paroxetin, trazodone, viloxazine, fluphenazine, perphenazine, promethazine, thioridazine, triflupromazine, prothipendyl, tiotixen, chlorprothixen, pipamperone, pimozide, fenethyllin, trifluoperazine, thioridazine, oxazepam, alprazolam, clobazam, piracetam, melfalan, cyclophosphamide, trofosfamide, chlorambucil, lomustin, busilfan, prednimustin, mercaptopurine, thioguanine, hydroxycarbamide, altretamine, procarbazine, lisuride, methysergide, pizotifen, roxatidine, pirenzipine, proglumide, bromopride, pheniramine, dimethindene, tritoqualine, loratadine, doxylamine, mequitazine, dexchlorpheniramine, triprolidine, oxatomide, moxonidine, doxazosine, urapidil, dihydralazine, deserpidine, alprenolol, bupranolol, penbutolol, esmolol, ciliprolol, metipranolol, nadolol, quinapril, fosinopril, cilazapril, democlocycline, lymecycline, oxytetracycline, sulfamethopyrazine, aerosoxacine, becampicillin, piperacillin, pivampicillin, cloxacillin, flucloxacillin, metronidazol, clindamycin, cefaclor, cefpodoxime, cephalexin, cefradin, pirbuterol, orciprenalin, clenbuterol, procaterol, choline theophyllinate, theophylline, ethylenediamine, ketofen, viquidil, procainamide, mexiletin, tocainid, ipratropium, tobutamide, gliquidon, gliboruride, tolazamide, acarbose and pharmaceutically active salts or esters of the aforementioned active substances as well as combinations of two or more of these active substances or their salts or esters.

Other suitable active substances include, for example, acebutolol, acetylcysteine, acetylsalicylic acid, aciclovir, albrazolam, alfacalcidol, allantoin, allopurinol, ambroxiol, amikacin, amiloride, aminoacetic acid, amiodaron, amitriptylin, amlodipin, amoxicillin, ampicillin, ascorbic acid, aspartam, astemizole, atenolol, beclometason, benserazide, benzalkonium hydrochloride, benzocaine, benzoic acid, betametasone, bezafibrate, biotin, biperidene, bisoprolol, bromacepam, bromhexine, bromocriptine, budesonide, bufexamac, buflomedil, busprione, caffeine, camphor, captopril, carbamacipine, carbidopa, carboplatin, cefaclor, cefalexin, cefadroxil, cefazolin, cefixime, cefotaxim, ceftazidin, ceftriaxon, cefuroxim, celedilin, chloramphenicol, chlorhexidine, chlorpheniramine, chlortalidone, choline, ciclosporin, cilastatin, cimetidine, ciprofloxacin, cisaprid, cisplatin, clarithromycin, clavulanic acid, clomibramin, clonazepam, clonidine, clotrimazole, codeine, cholestyramine, cromoglicinic acid, cyanocobalamin, cyproteron, desogetrel, dexamethason, dexpanthenol, dexthromethorphan, dextropropoxiphen, diazepam, diclofenac, digoxin, dihydrocodeine, dihydroergotamine, dihydroergototoxin, diltiazem, diphenhydramine, dipyridamol, dipyrone, disopyramide, domperidon, dopamine, doxcycline, enalapril, ephedrine, epinephrine, ergocalciferol, ergotamine, erythromycin, estradiol, ethinylestradinol, etoposid, famotidin, felodipin, fenofibrate, fenoterol, fentanyl, flavin mononucleotide, fluconazol, flunarizin, fluorouracil, fluoxetin, flurbiprofen, furosemide, gallopamil, gemfibrozil, gentaminicin, ginkgo biloba, glibenclamide, glipizid, glozapine, glycyrrhiza glabra, griseofulvin, guaifenesin, haloperidol, heparin, hyaluronic acid, hydrochlorothiazide, hydrocodon, hydrocortisone, hydromorphone, ibratropium hydroxide, ibuprofen, imipenem, indomethacin, iohexol, iopamidol, isosorbid dinitrate, isosorbid mononitrate, isotretionin, ketotifen, ketoconazol, ketoprofen, ketorolac, labatalon, lactulose, lecithin, levocarnitin, levodopa, levoglutamide, levonorgestrel, levothyroxin, lidocaine, lipase, lipramin, lisinopril, loperamid, lorazepam, lovastatin, medroxyprogesterone, menthol, methotrexate, methyldopa, methylprednisolone, metoclopramide, metoprolol, miconazol, midazolam, minocyclin, monoxidil, misoprostol, morphine, multivitamins and minerals, N-methylephedrine, naftidrofuril, naproxen, neomycin, nicardipin, nicergolin, nicotinamide, nicotine, nicotinic acid, nifedipin, nimodipin, nitrazepam, nitrendipin, nizatidin, norethisteron, norfloxacin, norgestrel, nortriptylin, nystatin, ofloxacin, omeprazol, ondansetron, pancreatin, panthenol, pantothenic acid, paracetamol, penicillin G, penicillin V, phenobarbital, phenoxifyllin, phenoxymethylpenicillin, phenylephrin, phenylpropanolamine, phenytoin piroxicam, polymxyxin B, povidine-iodine, pravastatin, prazepam, prazosin, prednisolone, prednisone, propafenone, propranolol, proxyphyllin, pseudoephedrine, pyridoxine, chinidin, ramipril, ranitidin, reserpine, retinol, riboflavin, rifampicin, rutosid, saccharin, salbutamol, salcatonin, salicylic acid, simvastatin, somatropin, sotalol, sprironolactone, sucralfate, sulbactam, sulfamethoxazole, sulfasalazin, sulpirid, tamoxifen, tegafur, teprenon, terazosin, terbutalin, terfenadin, tetracycline, theophylline, thiamine, ticlopidin, timolol, tranexamic acid, tretinoin, triamcinolone acetonide, triamteren, trimethoprim, troxerutin, uracil, valproic acid, vancomycin, verapamil, vitamin E, zidovudine.

Additional examples of suitable active substances that may be released from the multi-layer film according to the invention include proclorperazine edisylate, iron II sulfate, aminocaproic acid, potassium chloride, mecamylamine hydrochloride, procainamide hydrochloride, amphetamine sulfate, benzphetamine hydrochloride, isoporterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformine hydrochloride, methyl phenidate hydrochloride, oxprenolol hydrochloride, metroprolol tartrate, cimetidine hydrochloride, diphenidol, meclizine hydrochloride, proclorperazine maleate, phenoxybenzamine, thiethylperazine maleate, anisindone, diphenadione, erythritol tetranitrate, dizoxin, isofurophate, acetazolamide, methazolamide, bendroflumethiazide, chlorpropamide, tolazamide, chlormadinone acetate, phenaglycodol, aluminium aspirin, methotrexate, acetylsulfioxazole, progestins, estrogen steroids, progestatin steroids, corticosteroids, 17-β-oestradiol, ethinyloestradiol-3-methyl ester, hydrocorticosterone acetate, methyltesterone, 17-α-hydroxyprogesterone acetate, 19-norprogesterone, norethindrone, progesterone, norgesterone, norethynodrel, etc.

Examples of still more active substances that may be released with the aid of the multi-layer film of the invention include fenoprofen, sulindac, indoprofen, nitroglycerin, timolol, alprenolol, imipramine, chlorpromazine, dihydroxyphenylalanine, pivaloxyloxyethyl ester of α-methyldopa hydrochloride, calcium gluconate, iron II lactate, vincamin, phenoxybenzamine, blockers, etc. The active substances are known from "Pharmaceutical Sciences" by Reminston, 14th Edition, 1979, Mack Publishing Co., Easton, Pa.; "The Drug, The Nurse, The Patient, Including Current Drug Handbook", 1974–1976, by Falconer et al., Saunder Co., Philadelphia, Pa., and "Medical Chemistry", 3rd Edition, Vols. 1 and 2, by Burger, Wiley Interscience, New York.

Representative medicaments that may be administered to warm-blooded animals, for example ruminants, with the aid of the release system according to the invention include, inter alia, anthelmintics such as mebendazol, levamisol, albendazol, cambendazol, fenbendazol, parbendazol, oxfendazol, oxybendazol, thiabendazol, tichlorfon, praziquantil, morantel and pirantel, etc.; antiparasitic agents such as avermectine and ivermectin, as are disclosed in U.S. Pat. Nos. 4,199,569 and 4,389,397 (Merck) and in "Science", Vol. 221, pp. 823–828, 1983, where these ivermectin antiparasitic agents are said to be suitable to assist in controlling worms such as roundworms (maw-worms), lung worms etc. that commonly occur in mammals, and also that ivermectin is suitable for treating infestation by insects such as maggots, lice, mite mange, etc.; antimicrobial agents such as chlortetracycline, oxytetracycline, tetracycline, gentamicin, streptomycin, dihydrostreptomycin, bacitracin, erythromycin, ampicillins, penicillins, cephalosporins, etc.; sulfur-containing medicaments (sulfa drugs) such as sulfamethazine, sulfathiazole, etc.; growth stimulators such as Monesin® sodium and Elfazepam®; de-fleaing agents such as dexamethazone and flumethazone; agents and ionophores influencing digestion in stomachs of ruminants, such as lasalocid, virginamycin, salinomycin and ronnel; minerals such as copper oxide, cobalt sulfate, potassium iodate, zinc oxide, manganese sulfate, zinc sulfate, selenium, sodium selenite, beneficial mineral salts, etc.; antiswelling agents such as organic polysiloxanes; hormone growth additives such as stilboestrol; vitamins such as vitamins A and D with 500,000:100,000 IU/f, vitamin E with 500,000 IU/f, etc.; anti-enteritis agents such as furazolidone, growth factors, nutrient additives such as lysine monohydrochloride, methionine, magnesium carbonate, etc.; β-agonists, elenbuterol, etc. and chemical labelling substances such as chromium oxide, and salts of ytterbium and erbium.

Suitable locally-acting pharmaceutically active substances also include fungicides such as amphotericin B, antibiotics such as penicillins, cephalosporins, erythromycin, tetracycline, aminoglucosides, antiviral compounds such as acyclovir, idoxuridin, respiratory improvers such as chlorophyll, compounds inhibiting tissue growth, anticaries compounds such as metal fluorides, in particular sodium monofluorophosphate, tin fluoride, aminofluoride, painkillers such as methyl salicylate, local anaesthetics such as benzocaine, oral antiseptics such as chlorhexidine and its salts, hexylresorcinol, dequalinium chloride, cetylpyridine chloride, anti-inflammatory agents, hormones such as oestriol, anti-plaque compounds such as chlorhexidine and its salts, octenidine, or mixtures of thymol, menthol, methyl salicylate, eucalyptol, buffer compounds such as calcium phosphate, calcium carbonate, sodium bicarbonate, sodium and calcium hydroxide, as well as desensitisers for teeth, such as for example calcium nitrate.

Suitable active substances furthermore include disinfectants such as chlorine compounds, in particular calcium hypochlorite, an insecticide, pesticide, herbicide, fungicide or growth promoter, or fertilisers such as for example nitrogen-containing compounds, in particular urea/formaldehyde compounds, calcium nitrate, calcium sulfate, calcium chloride, ammonium nitrate, ammonium sulfate, monoammonium phosphate, dibasic ammonium phosphate, ammoniumphosphoric acid compounds, trace elements for foodstuffs, such as iron, zinc, manganese, copper, boron, molybdenum or mixtures thereof.

Active substances that are suitable for the production of the transdermal systems according to the invention also include steroid hormones such as:

Gestagen-active steroid hormones, such as for example 13-ethyl-17β-hydroxy-18,19-dinor-17α-pregn-4-en-20yl-3-one, 13-ethyl-17β-hydroxy-18,19,-dinor-17α-pregna-4,15-dien-20yn-3-one (=Gestoden), 13-ethyl-17β-hydroxy-11-methylene-18,19-dinor1-17α-pregn-4-en-20yne or 13-ethyl-11-methylene-17β-hydroxy-18,19,-dinor-17α-pregn-4-en-3-one (3-keto-desogestrel), estrogen-active steroid hormones, e.g. 3-hydroxy-1,3,5-(10)-estratriene-17-one (=Estron), 1,3,5(10)-estratriene-3,17β-diol or 1,9-nor-17α-pregna-1,3,5(10)-trien-20yn-3,17β-diol, 17β-hydroxy-19-nor-17α-pregn-4en-20yn-3-one, 14α, 17α-ethano-1,3,5 (10)-estratriene-3,17β-diol (=Cyclodiol) and 14β, 17α-ethano-1,3,5(10)-estratriene-3,16α,17β-triol (=Cyclotriol) and combinations of these gestagens and estrogens.

Androgen-active steroid hormones such as 17β-hydroxy-4-androsten-3-one (=testosterone) and its esters, or 17β-hydroxy-1α-methyl-5α-androsten-3-one (=mesterolone).

Anti-androgen active steroid hormones such as 17α-acetoxy-6-chloro-1β,2β-dihydro-3H-cyclopropa[1,2]-pregna-1,4,6-triene-3,20-dione.

Corticoids such as 11β,17α,21-trihydroxy-4-pregnene-3,20-dione, 11β,17α,21-trihydroxy-1,4-pregnadiene-3,20-dione, 11β,17α,21-trihydroxy-6α-methyl-1,4-pregnatriene-3,20-dione, and 6α-fluoro-11β,21-dihydroxy-16α-methyl-1,4-pregnadiene-3,20-dione (=diflucortolone) and their esters.

Suitable active substances additionally include:

Ergolin derivatives such as the lisuride, [3-(9,10-didehydro-6-methyl-8α-ergolinyl)-1,1-diethylurea], the bromolisuride [=3-(2-bromo-9,10-dehydro-6-methyl-8α-ergolinyl-1,1-diethylurea], the terguride [=3-(6-methyl-8α-ergolinyl-1,1-diethylurea], and the proterguride [=3-(6-propyl-8α-ergolinyl)-1,1-diethylurea].

Antihypertensive agents such as 7α-acetylthio-17α-hydroxy-3-oxo-4-pregnen-21-carboxylic acid-γ-lactone and 7α-acetylthio-15β-, 16β-methylene-3-oxo-17α-pregna-1,4-diene-21,17-carbolactone (=mespirenon).

Anticoagulants such as 5-[hexahydro-5-hydroxy-4-(3-hydroxy-4-methyl-1-octen-6-ynyl)-2(1H)-pentalenylidene)]-pentanoic acid (=iloprost) or (Z)-7-[(1R,2R,3R,5R)-5-chloro-3-hydroxy-2-[(E)-(3R)-3-hydroxy-4,4-dimethyl-1-octenyl]-cyclopentyl]-5-heptenoic acid (=nocloprost).

Psychopharmaceuticals such as 4-(3-cyclopentyloxy-4-methoxyphenyl-2-pyrrolidone (=rolipram) and 7-chloro-1,3-dihydro-1-methyl-5-phenyl-2H-1,4-benzodiazepin-2-one.

The multi-layer film according to the invention preferably may contain up to 30% of active substance, relative to the weight of the film itself, without affecting the mechanical properties of the multi-layer film.

The adherent layer, adapted to the application site, is applied directly to the active substance-containing layers. According to the invention the adherent layer may consist essentially of non-crosslinked, preferably mucoadhesive, polymers. Particularly preferred polymers for forming the adherent layer include polyacrylic acid (Carbopol 934 P, ca. 80%) and methylcellulose (Metholose 90 SH 100, ca. 20%). The thickness of the adherent layer film is preferably 5–50 μm, particularly preferably 10–30 μm.

The multi-layer film according to the invention is suitable in particular for use as a transmucosal medicament form. Such use is therefore also embraced within the scope of the present invention.

The multi-layer film according to the invention is preferably produced by building up the layers on top of one another on a preferably smooth surface, by applying the film-forming polymers and optionally the crosslinking agent and optionally the active substance per layer in each case by spraying and drying in partial layers. Preferably each layer is built up from 0.1–10 μm thick partial layers. The drying stage is preferably carried out simultaneously with the spraying.

Aqueous solutions are preferably used as solutions. The spraying of the film-forming, aqueous polymer solution and the spraying of the crosslinking agent, present as an aqueous solution, of the cover layer and active substance-containing layer(s) are preferably carried out simultaneously, the polymer solution and the crosslinking agent being mixed after the spraying and crosslinked in situ.

The incorporation of the active substance into the active substance-containing layer is preferably carried out by dissolving the active substance(s) or, if necessary, emulsifying and/or suspending the active substance(s) in the form of liquid or solid particles in the aqueous solutions of the crosslinking agent. It is particularly advantageous in this connection to incorporate solids into the polymer solution, which thereby serves as a suspension stabiliser for the spraying.

Partial layers of the active substance-containing layer with different active substance concentrations and/or different active substances can be produced by changing the solution that is sprayed from the nozzles. Local, optionally different concentrations of active substances within an active substance-containing layer are produced by operating the respective nozzles with different, optionally variously concentrated solutions.

The spraying of the respective substances required for the production of the multi-layer film according to the invention is carried out with single-component and/or two-component nozzles whose spray cones overlap. The smooth surface on which the multi-layer film is built up is preferably moved cyclically underneath the spray cones.

In order to produce the multi-layer film according to the invention with as uniform a thickness as possible, it is advantageous if the spray cones overlap, and the smooth surface on which the multi-layer film is built up preferably moves cyclically underneath the nozzles.

The high degree of variability of the process according to the invention enables the layer build-up to be carried out in the reverse sequence. Thus, it is also possible to start with the adherent layer as the initial substrate for the successive active substance-containing layers and cover layer on the support surface.

The application of more than three layers is also possible without any problem by means of the process according to the invention. Thus, an additional barrier layer applied to the release side and that is free of active substance may serve for the delayed release of otherwise rapidly released active substances.

The multi-layer film according to the invention can best be produced using a device that comprises at least one spray means, a dryer and at least one plate that is moved cyclically underneath the spray means. This device is accordingly also covered by the present invention. Preferably the device has a plurality of nozzles whose spray cones overlap.

The multi-layer film according to the invention is simple to produce and is not environmentally harmful since aqueous solutions are employed. The multi-layer film adheres for example extremely well even over a prolonged period to the mucous membrane of the mouth. Patients in whose mouth cavity the multi-layer film according to the invention has been used experience only a very slight sensation of a foreign body.

Multi-layer films with an arbitrary layer combination can be produced simply and very precisely by means of the process according to the invention.

The multi-layer film according to the invention and the process according to the invention for producing such a multi-layer film are described in further detail hereinafter with reference to illustrative examples, which, however, are not intended to limit the scope of the invention.

EXAMPLE 1

Mucoadhesive Multi-layer Film Free of Active Substance

The following are employed to produce 50 g of film having a surface area of 3472 cm$^2$, corresponding to 771 film pieces each of 4.5 cm$^2$ surface area:

a. Cover layer: 835 g of a 2% solution of 16.7 g of MHPC 100 and 819 g of water, as well as 835 g of a 0.5% solution of 4.17 g of tannin and 831 g of water; resultant layer thickness of the partial film 50 µm.
b. Middle layer potentially suitable for absorbing active substance: 835 g of a 2% solution of 16.7 g of MHPC 100 and 819 g of water, as well as 835 g of a 0.5% solution of 4.17 g of tannin and 2.35 g of Carbopol 934 P; resultant layer thickness of the partial film 50 µm.
c. Adherent layer: 842 g of a 1% solution of 1.67 g of Metholose 90 SH 100, 6.67 g of Carbopol 934 P and 833 g of water; resultant layer thickness 20 µm.

The aqueous solutions of the polymers are prepared by stirring the polymer powders in purified water that has been heated to 80° C., following by cold stirring at room temperature with a blade stirrer. The necessary solutions—namely polymer and crosslinking agent—for the cover layer and middle layer are fed by hose pumps in a conveyed amount of 2.5 g/min$^{-1}$ and sprayed through nozzle openings of size in each case 0.5 mm with an atomiser excess pressure of 1 bar onto glass plates spaced ca. 10 cm apart. The nozzles are adjusted so that the cones of the spray jets overlap on the glass supports. In order to produce an homogeneous distribution of the film mass, the glass supports are cyclically moved at a uniform speed underneath the spray jet, which is achieved by fixing the glass supports to the drum of a pelletising plate rotating at constant speed. Up to 0.5 µm thick film layers can be sprayed in one cycle. The spraying rate and the number of cycles accordingly determine the thickness of a partial layer. The sprayed films are dried simultaneously by feeding in dry air at a temperature of at most 60° C. The individual layers are produced immediately after one another by changing the spray solutions.

After the drying stage the overall film can easily be removed from the glass supports. The film has a thickness of 120 µm±4 µm. The mean adhesion times of the multi-layer film in the mouth cavity are:

| | |
|---|---|
| gingival: | 470 min. |
| palatal: | 210 min. |
| buccal: | 120 min. |

At the end of the application the multi-layer films according to the invention can easily be removed as whitish, swollen discs.

EXAMPLE 2

Multi-layer Film With 1% Prednisolone

The following are employed for the production of 50 g of film having a surface area of 3439 cm$^2$, corresponding to 764 film pieces each of surface area 4.5 cm$^2$:

a. Cover layer: 825 g of a 2% solution of 16.5 g of MHPC 100 and 809 g of water, as well as 825 g of a 0.5% solution of 4.1 g of tannin and 821 g of water; resultant layer thickness 50 µm.
b. Active substance-containing layer: 825 g of a 2% solution of 16.5 g of MHPC 100, 0.48 g of finely dispersed prednisolone and 808 g of water, as well as 825 g of a solution of 4.1 g of tannin and 821 g of water; resultant layer thickness 50 µm.
c. Adherent layer: 833 g of a 1% solution of 6.67 g of Carbopol 934 P, 1.67 g of MHPC 100 and 825 g of water; resultant layer thickness 20 µm.

The production is carried out as described in Example 1. For the build-up of the active substance-containing layer, as a departure from Example 1 a 2% MHPC solution is used in which micronised prednisolone is suspended by being stirred in during the cooling phase of the solution. The overall film thickness after drying is 120 µm±4 µm.

EXAMPLE 3

Multi-layer Film With 1.3% Prednisolone and Strengthened Cover Layer

The following are used to produce 50 g of film having a total surface area of 3069 cm$^2$, corresponding to 682 film pieces each of 4.5 cm$^2$ surface area:

a. Cover layer: 937 g of a 2% solution of 18.73 g of MHPC 100 and 918 g of water, as well as 937 g of a 0.5% solution of 4 g of tannin and 933 g of water; resultant layer thickness 64 µm.
b. Active substance-containing layer: 737 g of a 2% solution of 14.73 g of MHPC 100, 0.65 g of finely dispersed prednisolone and 722 g of water, as well as 737 g of a 0.5% solution of 3.86 g of tannin and 734 g of water; resultant layer thickness 50 µm.
c. Adherent layer: 736 g of a 1% solution of 5.89 g of Carbopol 934 P, 1.47 g of MHPC 100 and 729 g of water; resultant layer thickness 20 µm.

The production is carried out as described in Example 1 or Example 2. The film thickness of the overall film after drying is 134 µm±5 µm.

EXAMPLE 4

Multi-layer Film With 4.6% Prednisolone

The following are used to produce 50 g of film having a total surface area of 3314 cm², corresponding to 736 film pieces each of 4.5 cm² surface area:

a. Cover layer: 796 g of a 2% solution of 15.91 g of MHPC 100 and 780 g of water, as well as 796 g of a 0.5% solution of 4 g of tannin and 792 g of water; resultant layer thickness 50 μm.
b. Middle layer: 796 g of a 0.5% solution of 15.91 g of MHPC 100, 2.29 g of finely dispersed prednisolone and 778 g of water, as well as 796 g of a 0.5% solution of 4 g of tannin and 792 g of water; resultant layer thickness 50 μm.
c. Adherent layer: 795 g of a 1% solution of 6.3 g of Carbopol 934 P, 1.59 g of MHPC 100 and 787 g of water; resultant layer thickness 20 μm.

The film was produced as described in Example 2. The layer thickness of the overall film is 120 μm±5 μm.

In in vivo tests, the multi-layer films according to the invention described above with Carbopol 934 P and Metholose 90 SH 100 as adherent layer exhibit an unexpectedly good adhesion capability to different application sites in the oral cavity, the patients experiencing scarcely any sensorial impression of a foreign body.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A multi-layer film of film-forming polymers comprising a cover layer, at least one layer containing an active substance, and an adherent layer, wherein the active substance-containing layer comprises hydrophilic polymers crosslinked in situ, and wherein at least one active substance-containing layer has a horizontal and/or vertical gradient as regards the active substance, or the active substance is concentrated in specific horizontal and/or vertical segments of the active substance-containing layer.

2. A multi-layer film according to claim 1, wherein the cover layer is comprised of hydrophilic polymers crosslinked in situ.

3. A multi-layer film according to claim 1, wherein the cover layer and the active substance-containing layer are each from 30 to 100 μm thick.

4. A multi-layer film according to claim 1, wherein said hydrophilic polymers are cellulose ethers crosslinked with a phenolic substance.

5. A multi-layer film according to claim 4, wherein said hydrophilic polymers are selected from the group consisting of hydroxyethyl-cellulose, methylcellulose and methylhydroxypropylcellulose.

6. A multi-layer film according to claim 4, wherein said hydrophilic polymers are composed of methylhydroxypropylcellulose crosslinked with tannin.

7. A multi-layer film according to claim 1, wherein said hydrophilic polymers are anionic polymers.

8. A multi-layer film according to claim 7, wherein said hydrophilic polymers comprise anionic polymers selected from the group consisting of sodium carboxymethylcellulose, polyacrylates and carragenates, that have been crosslinked with inorganic ions or with polycations.

9. A multi-layer film according to claim 8, wherein said hydrophilic polymers comprise sodium alginate crosslinked with calcium ions or chitosan.

10. A multi-layer film according to claim 1, wherein the cover layer further comprises at least one auxiliary substance selected from the group consisting of colorants and flavoring agents.

11. A multi-layer film according to claim 1, wherein said adherent layer comprises methylhydroxypropylcellulose and polyacrylic acid.

12. A multi-layer film according to claim 1, wherein the film contains a plurality of active substances.

13. A multi-layer film according to claim 12, wherein each active substance-containing layer contains at least one active substance.

14. A multi-layer film according to claim 1, wherein the film contains at least one active substance selected from the group consisting of aromas, plant protection agents, pharmaceutically active agents, vitamins, nutrients, and fertilizers.

15. A method of transmucosally administering a medicament to an organism comprising applying a medicament-containing, multi-layer film according to claim 1, to a mucosal membrane of said organism.

16. A process for producing a multi-layer film according to claim 1, comprising applying a plurality of layers successively on a smooth surface, wherein each successive layer is formed by spraying respective partial layers of solutions containing the film-forming polymer, the crosslinking agent and at least one active substance on one another on said smooth surface followed by drying.

17. A process according to claim 16, wherein the cover layer and the at least one active substance-containing layer are each produced by simultaneously spraying a solution of film-forming polymer and the crosslinking agent on the surface.

18. A process according to claim 16, wherein the spraying is carried out using at least one single-component, two-component or three-component nozzle.

19. A process according to claim 16, wherein the at least one active substance sprayed on dissolved or emulsified or suspended in an aqueous solution of the crosslinking agent.

20. A process according to claim 16, wherein the solutions containing the film-forming polymer, the crosslinking agent and at least one active substance are sprayed onto a plate on top of one another by spray cones which overlap, and the plate is cyclically moved underneath the spray cones.

* * * * *